April 22, 1952 C. H. HUNKEL Plant Pat. 1,085
POINSETTIA PLANT
Filed Feb. 20, 1951
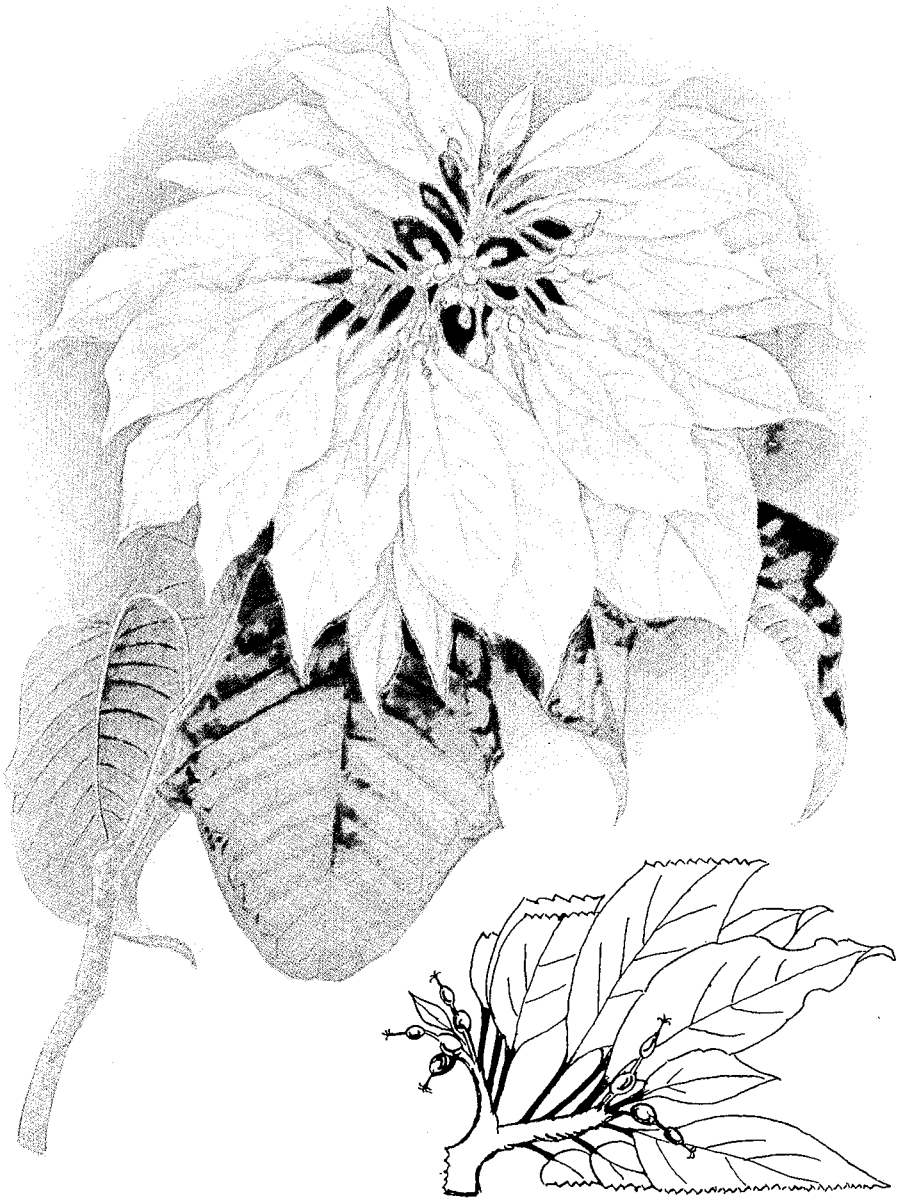
WITNESS
Addison E. Avery
INVENTOR
CAROL H. HUNKEL,
by Rummler, Rummler & Snow,
ATTYS.

Patented Apr. 22, 1952

Plant Pat. 1,085

UNITED STATES PATENT OFFICE 1,085

POINSETTIA PLANT

Carol H. Hunkel, Milwaukee, Wis., assignor to Holton & Hunkel Co., Milwaukee, Wis., a corporation of Wisconsin Application February 20, 1951, Serial No. 211,830

1 Claim. (Cl. 47—60)

The subject of the present application is a new and distinct variety of poinsettia, being a descendent of *Euphorbia pulcherrima*, a shrub of tropical America that was introduced into the United States and through the years has been much improved by development and cultivation. The present specific variety originated as a sport of Ecke's white poinsettia and was discovered in my greenhouse at Milwaukee, Wisconsin. The new variety has been reproduced asexually from cuttings through several generations at my greenhouse at Brown Deer, town of Granville, Milwaukee County, Milwaukee, and its characteristics appear to be permanently fixed.

Its most outstanding feature of novelty resides in the smooth creamy white coloring and abundance of its bracts, which are not merely double but lie in a dense cluster, three or four layers deep, of large bracts and a single row of bractlets, surrounding an open central space that is spanned by radiating green branches studded with minute but brilliantly orange colored flowers.

In the accompanying drawing, which forms a part of this application, the painted main figure illustrates the form and color distribution in the new variety when its bloom is mature, and the small pen and ink sketch illustrates the manner in which the bract-bearing and flower-bearing stalks branch out from the tip of the stem.

The following is a detailed description of the new variety:

*Structure*

In general plant structure, this variety is similar to the well-known poinsettias but resembles the red varieties more than the white ones. Compared with some varieties, it is short and squatty, being about 18 to 20 inches tall and the plant is about as wide as it is tall. The stems are stiff and very strong.

The length of the stems is about 15 inches and the internodes are very short. The tip of each stem is crowned by a cluster of laterally disposed short and thick branches radiating from a common node, these being the peduncles of the flower clusters, which branch into numerous bract-stalks and pedicels.

*Foliage*

The quantity of leaves is about normal but appears to be more abundant than usual because of the short internodes. The leaves are thick, tough, and heavily veined, about 4 inches in length, 2 inches in width and panduriform in shape, being on the average somewhat smaller than those of the red varieties of poinsettia. The petioles are long and curved and branch singly from the stem in spiral arrangement. The leaves hold on to the stem tenaciously under various conditions.

*Bracts*

The largest of the bracts are somewhat similar to the leaves in form except that they are small, softer in texture, more lanceolate in contour and entirely different in color, being creamy white in contrast to the green leaves. The bract-stems are of about the same color and texture as the petals. They are arranged 3 or 4 in succession along the peduncles and in the aggregate form a wreath-like whorl of multiple layers of petals approximately 9 inches in diameter, surrounding a central open space occupied by a lacework of branches with scattered flowers of the clusters.

*Flowers*

The flowers are tiny, orange-red in color, borne in three or four clusters of widely spaced florets. Each pedicel has two seed pods in tandum arrangement thereon.

The flower buds are small and globular in shape. The cups of the flowers are green and before maturity bearded. As they open, they are orange-red in color. Stamens and pollen are yellow but do not appear in the painting which shows the bloom at a late stage.

*Appearance*

As is brought out in the painting, the flowers are orange-red in color and arranged in a cluster of tiny florets scattered widely apart like jewels on a lacework of light green branches, spanning an open central space which is surrounded by a dense wreath-like mass of creamy white bracts at the top of a stem bearing sharply contrasting dark green leaves. On the whole the appearance of the plant is conspicuously outstanding and strikingly beautiful.

*Habits*

The growth is vigorous and the stems branch readily when pinched back.

The plant is a profuse bloomer, blooming 10 days to 2 weeks earlier than the parent stock, being in full flower by December 1st, and has to be held back for the Christmas trade. Its keeping qualities are exceptional, lasting in the greenhouse about 90 days. During the last season they were in bloom from Christmas until March.

Color identification according to Maerz & Paul is charted below.

| | Plate | Letter | No. |
|---|---|---|---|
| Small Bract Petals | 17 | L | 3 |
| Large Bract Petals | 17 | E | 1 |
| | 17 | H | 1 |
| Foliage leaves, top side | 19 | L | 8 |
| Foliage leaves, under side | 19 | F | 6 |

Having thus disclosed the invention, I claim:

A new and distinct variety of poinsettia plant, substantially as shown and described, characterized by its short stem internodes, and its distinctive coloring and arrangement of multiple layers of creamy white bracts.

CAROL H. HUNKEL.

No references cited.